United States Patent [19]

Gilbert

[11] Patent Number: 4,869,093

[45] Date of Patent: Sep. 26, 1989

[54] METHODS AND APPARATUS FOR DETERMINING SORPTION ISOTHERMS

[75] Inventor: Seymour G. Gilbert, Piscataway, N.J.

[73] Assignee: Rutgers, The State University, Piscataway, N.J.

[21] Appl. No.: 195,505

[22] Filed: May 18, 1988

[51] Int. Cl.[4] .............................................. G01N 31/08
[52] U.S. Cl. ........................................ 73/23.1; 422/89
[58] Field of Search ..................... 73/23.1, 27; 422/89; 436/161; 55/386, 67

[56] References Cited

U.S. PATENT DOCUMENTS 3,607,075  9/1971  Wolf et al. ............................ 73/23.1
3,879,568  4/1975  Luh et al. ............................. 426/465
4,003,257  1/1977  Fletcher et al. ...................... 73/23.1

OTHER PUBLICATIONS

Paik et al., *J. of Chromatogr.*, 351 (3) 417–423, (1986).

*Primary Examiner*—Hezron E. Williams
*Attorney, Agent, or Firm*—Lerner, David, Littenberg, Krumbolz & Mentlik

[57] ABSTRACT

A method for determining sorption isotherms of food by inverse chromatography comprising the steps of passing a mobile phase having a known solute concentration and at a known flow rate through a stationary phase comprising a known mass of food at a known temperature, measuring the concentration of solute in the mobile phase leaving the food, determining the amount of solute which has entered the food at selected intervals from the known concentration, known flow rate and time elapsed from the beginning of the passing step, determining the amount of solute which has passed downstream of the food at selected intervals from the measurement of the concentration of the solute, and determining the amount of solute at selected intervals taken up by the food from the difference in the amounts determined above.

19 Claims, 1 Drawing Sheet

METHODS AND APPARATUS FOR DETERMINING SORPTION ISOTHERMS

FIELD OF THE INVENTION

This invention relates to a method and apparatus for determining sorption isotherms of food.

BACKGROUND OF THE INVENTION

Interactions of low molecular weight molecules with food are an integral part of food science. Among the most important interactions are those involving water with carbohydrates and proteins. This insertion also affects food components such as vitamins and enzymes. Equilibrium studies in the form of sorption isotherms are particularly useful for evaluating the thermodynamics of these interactions.

A sorption isotherm is essentially a set of data defining the relationship at a particular temperature between solute vapor pressure in the surroundings and solute content of the food at equilibrium. Most of the methods which are used to determine sorption isotherms are gravimetric (static methods) and are based upon equilibration of the sample over time at constant vapor pressure and temperature. These methods usually require long periods of time to achieve equilibrium, and require numerous repeated experiments at different vapor pressures to develop the full set of data constituting the isotherm.

Inverse gas chromatography (IGC) has also been used to determine sorption isotherms of food. The advantages of using this approach are that small samples of materials may be used, sorption data may be determined quickly, and the sensitivity of the method in the low vapor pressure region is very good. Inverse chromatography is a test method wherein a fluid or "mobile phase" bearing the solute is passed through the solid or stationary phase material to be studied. The properties of the stationary phase are deduced from observations of the solute content in the mobile phase leaving the solid. In inverse gas chromatography the mobile phase is a gas. The use of specific vapor detectors, such as thermal conductivity, flame ionization and mass spectrometry, greatly enhances the specificity and sensitivity of the method.

The inverse gas chromatography method is sensitive to the rate of sorption of water vapor and measures kinetic effects which tend to be obscured in the long term gravimetric method. Sorption can be controlled in an inverse gas chromatography experiment by varying the factors contributing to contact efficiency thereby producing insights into the structure of the solid phase and into non-equilibrium sorption rate. A study with the gravimetric method reveals that this static method may not yield a final equilibrium sorption value. Instead, the gravimetric method stops at a point where the rate of water vapor sorption to achieve the remaining sorption equilibrium differential has slowed down to the point where a gravimetric determination shows no measurable gain in weight, a function of the sensitivity of the method.

The two major types of inverse chromatography are frontal analysis and pulse (elution) analysis. In frontal inverse chromatography, the entire sample of solute is introduced continuously into the column. Frontal chromatography may be divided into sorption and desorption phases. When a constant supply of mobile phase with a defined single solute concentration is supplied to a column, there is an initial delay in transit because of solute sorption. This period of delay is followed by a period of increasing solute concentration in the stationary phase which produces a corresponding rise in solute concentration in the mobile phase leaving the column until both phases are saturated in equilibrium with the input concentration. Consequently the exit concentration reproduces the sorption isotherm for the range of the input partial pressure of the solute. The subsequent passage of pure mobile phase produces the desorption isotherm.

In elution chromatography, an initial concentration of solute is introduced into a column of sorbant followed by pure mobile phase. An individual component is eluted from the column as a distinct peak as a result of the selective retardation of that component by the stationary phase. The peak formed on exit has an area proportional to the injected mass and a retention time related to the partition coefficient of the equilibrium zone.

The frontal inverse chromatography sorption method provides satisfactory agreement with static or long term equilibrium studies but requires a series of maintained solute concentrations to cover the full sorption isotherm range. The longer equilibrium periods required in frontal inverse chromatography, as compared to elution inverse chromatography, also require more elaborate controls of the chromatographic conditions. The pulse or elution sorption chromatography method, although not as accurate as frontal chromatography, has the advantages of rapidity and simplicity.

The height of the peak in the detector response is related to the partial pressure of the solute at any time. The area of the peak is proportional to the amount of solute injected, whereas the so-called "pre-peak area", and other parameters derived from the detector response versus time, is related to the amount sorbed. Since the calculations for the above two methods assumes equilibrium conditions, the validity of the methods requires ideal conditions, where equilibration is rapid compared to transit time. In order to achieve these conditions, the common practice is to use low concentrations of solute. Non-linear sorption isotherms, which rapidly attain equilibrium in the chromatographic transit time, can also be evaluated by inverse chromatography.

The period of the detector response before elution and after passage of a non-sorbed pulse, such as air, is referred to as the prepeak period. The area of the detector response during this prepeak period is proportional to the sorption at a pressure equivalent to a specific response height provided that there are no appreciable non-linear kinetic factors restricting elution. The response height is determined by the desorption phase. The prepeak time to any specific solute concentration in the gas phase is determined by the sorption phase.

Integrating detector response over the elution concentration profile provides prepeak and peak areas proportional to sorption and desorption only if there is a linear response of the detector to solute mass, and equilibrium is reversible and achieved in solute transit.

Differences in the proportionality constants between areas and heights for mass injected will produce corresponding discrepancies in the calculation of sorption isotherms. Such discrepancies result from the existence of nonlinear concentration relationships with hysteresis (nonequilibrium conditions) for cycles of sorption and desorption.

In conventional inverse chromatography, only the amount of effluent solute leaving the stationary phase is monitored. Incomplete elution of the solute from the stationary phase results in underestimation of both prepeak and peak area as well as partial solute pressure. The relation between height of the peak and vapor pressure, if not linear because of incomplete elution of solute, can be seriously in error at low pressure when calculated from linear calibration data. These errors tend to linearize sorption isotherms that are non-linear when determined by long term gravimetric studies.

The linear transport of a solute in the mobile gas phase isothermally through a column containing a stationary phase is characterized by a number of changes in the solute concentration created by diverse factors. First, there is a partition coefficient between the mobile and stationary phases which may vary from a simple concentration independent constant to a very complex, concentration dependent constant. Second, the relationship can be modified by kinetic effects. These effects include peak broadening as a result of solute diffusion in the stationary phase as well as in the void volume or carrier gas phase. This broadening is particularly significant when solid stationary phases are used as opposed to liquid or coated substrates.

In conventional chromatography, a relatively small mass of solute is injected as a sharp pulse into a large mass of solid phase in a long column. The pulse rapidly shifts from a sharp square wave shape into a Gaussian shape. The peak position and height are governed by thermodynamic interactions between the solute and substrate and the peak width is governed by diffusional effects. Selection of substrate and solute concentration, temperature and flow rate can often be achieved to obtain a relatively narrow band maximizing the thermodynamic parameters and minimizing diffusional ones.

One approach to the problem of non-ideal or nonequilibrium conditions is to use a post elution pulse of appropriately elevated temperature to elute the strongly bound solute as a peak area instead of as a diffuse nonquantifiable rear boundary at a lower temperature. Paik, S. W. and Gilbert, S. G., Water Sorption Isotherms of Sucrose and Starch by Modified Inverse Frontal Gas Chromatography, *J. of Chromatogr.* 351 (3), 417–423 (1986).

Thus, the modified frontal inverse chromatography desorption method provides satisfactory agreement with static or long term equilibrium studies but requires a series of maintained solute concentrations to cover the full sorption isotherm range. The advantages of rapidity and simplicity in pulse or elution chromatography method are hence not present.

Accordingly, there have been significant needs for improvements in methods and in the apparatus for determining sorption isotherms of food by inverse chromatography.

SUMMARY OF THE INVENTION

The present invention is directed to a method and an apparatus which utilize inverse chromatography to determine sorption isotherms of food.

One aspect of the present invention provides a method for determining sorption isotherms of food systems by inverse chromatography comprising the steps of (a) passing a mobile phase having a known solute concentration and at a known flow rate through a stationary phase comprising a known mass of the food at a known temperature, (b) measuring the concentration of the solute in the mobile phase passing downstream of the stationary phase, (c) determining the amount of the solute which has passed into the mass of the food at selected time intervals during the passing step from the known solute concentration, the known flow rate and the time elapsed since the beginning of the passing step, (d) determining the amount of the solute in the mobile phase which has passed downstream from the mass of food at each of said selected time intervals during the passing step from the measurements of the concentration of the solute in the mobile phase, and (e) determining the amount of solute taken up by the food at selected time intervals during the passing step from the difference in the amounts determined in steps (c) and (d).

Another aspect of this invention is directed at an apparatus for determining sorption isotherms of food by inverse chromatography. The apparatus includes a source of mobile phase, conduit means for conducting the flow of the mobile phase towards and away from a chromatograph, an injection port for introducing a known amount of a solute into the mobile phase, a chromatograph at a known temperature, a pre-column tubing disposed in the chromatograph for maintaining the solute pressure in the mobile phase at a constant saturated pressure and at a known flow rate, a column containing a stationary phase comprising food disposed in the chromatograph and a detector measuring means for measuring the amount of the solute in the mobile phase passing downstream of the food.

DETAILED DESCRIPTION OF THE INVENTION

Figure 1:
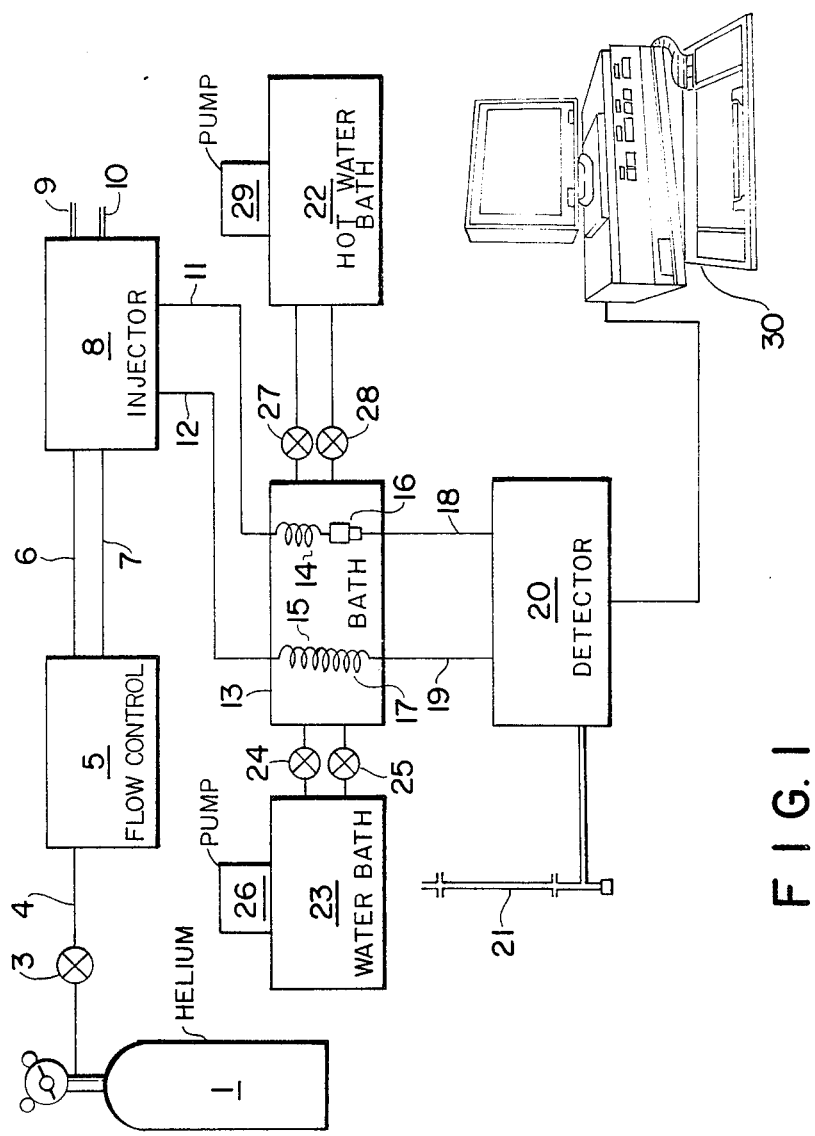
FIG. 1 is a schematic diagram of an apparatus used in one embodiment of the present invention.

One embodiment of the present invention is illustrated by the apparatus in FIG. 1. Helium tank 1 is equipped with a tank valve 2 and a pressure regulator valve 3. Valve 3 is adjusted to provide a stream of helium carrier gas (mobile phase) at a pressure of about 40 psig in conduit means 4 (⅛" O.D. copper tubing). Dual flow controller 5 splits the stream of carrier gas in conduit means 4 into two streams of carrier gas in conduit means 6 and 7. Conduit means 6 and 7 are connected to injection port 9 and injection port 10, respectively, each being disposed in injector 8.

Conduit means 11 connects injection port 9 to precolumn tubing 14 disposed in constant temperature bath 13. Pre-column tubing 14 is connected to experimental column 16 which in turn is connected to thermal conductivity detector 20 through conduit means 18. Similarly, conduit means 12 connects injection port 10 to pre-column tubing 15 also disposed in constant temperature bath 13. Pre-column tubing 15 is connected to empty column 17 which in turn is connected to detector 20 through conduit means 19. Conduit means 11 and 12 between constant temperature bath 13 and injector 8 and conduit means 18 and 19 between constant temperature bath 13 and thermal conductivity detector 20 are insulated at a level sufficient to prevent undue temperature fluctuations. The flow of carrier gas from detector 20 is vented through meter 21. The response data from detector 20 are collected over specific time intervals between samplings and is stored on the hard disk of computer 30 using conventional laboratory data logging software.

The temperature of constant temperature bath 13 is maintained by heated and cooled water bath 23. The temperature of the heated and cooled water in bath 23 is controlled by a conventional thermostat (not shown). Heated and cooled water is pumped from bath 23 to constant temperature bath 13 by pump 26. Mechanical valves 24 and 25 open and close the supply of heated and cooled water to bath 13. Constant temperature bath 13 may be a chamber (Hewlett Packard 5750 gas chromatograph) enclosing both experimental column 16 and empty column 17.

The temperature of constant temperature bath 13 may be pulsed by heated water bath 22. When the desorption curve has fallen to about 10% of the maximum peak height, experimental column 16 and empty column 17 may be subjected to a temperature pulse (bake-out condition at 70° C.) to remove tightly bound water from the stationary phase in experimental column 16. The temperature of the hot water in bath 22 is controlled by a conventional thermostat (not shown). Heated water is pumped from bath 22 to constant temperature bath 13 by pump 29. Mechanical valves 27 and 28 open and close the supply of heated water to bath 13.

In a method according to one embodiment of the invention, constant temperature bath 13 is maintained at the desired column temperature, typically 25°, 30°, 35° or 40° C. by heated and cooled water bath 23. Mechanical valves 24 and 25 are kept open whereas valves 27 and 28 are kept closed. Injection 8 is maintained at a predetermined vaporization temperature above 100° C. and typically about 150°–200° C. The oven surrounding thermal conductivity detector 22 is adjusted to a temperature of about 150° C. The thermal conductivity detector (TCD) is set at about 150 mA filament amperage. The Wheatstone bridge in the thermal conductivity detector is balanced. The laboratory data logging software parameters in computer 30 are set for conditions appropriate for the run. The time interval between data points is set at either 1/6 or 1/60 Hz.

A stream of carrier gas flows from belium tank 1 through conduit means 4 to dual flow controller 5. The gas flow rate is adjusted using a soap bubble film meter to about 40 cc helium/minute. Dual flow controller 5 splits the flow of carrier gas into a first stream and a second stream which flow through conduit means 6 and 7, respectively. The first stream of carrier gas flows to injector 8 wherein water is introduced into the stream through injection port 9. Because the injector 8 is at the relatively high vaporization temperature, the water introduced into port 9 vaporizes substantially instantaneously. The first stream of carrier gas bearing water vapor as a "spike" or bolus then flows from injection port 9 through conduit means 11 to pre-column tubing 14 disposed in constant temperature bath 13.

Because pre-column tubing 14 is at the relatively low column temperature maintained by bath 13, water vapor in the carrier gas stream condenses on the pre-column tubing so that the carrier gas stream flowing downstream through the pre-column tubing 14 comes to equilibrium at the column temperature. As carrier gas without water flows downstream through pre-column tubing 14 after the initial injection, the condensed water within the pre-column tubing evaporates, so that the carrier gas flowing downstream from the pre-column tubing remains saturated with water vapor at the column temperature until the water condensed in the pre-column tubing 14 is depleated.

The first stream of carrier gas flows from pre-column tubing 14 to experimental column 16 which contains food material (stationary phase) and then through conduit means 18 to thermal conductivity detector 20. The response from detector 20 is collected over a specific time intervals between samplings and is stored in computer 30.

In a similar manner, a trace or reference injection may be made for external calibration purposes into the empty column of exactly the same amount of water to be used in the corresponding run in the experimental column and under the same gas chromatographic operating conditions as the experimental run. Accordingly, a second stream of carrier gas flows through conduit means 7 to injector 8 where solute (water) is introduced through injection port 10. The second stream of carrier gas then flows from injection port 10 through conduit means 12 to pre-column tubing 15 disposed in constant temperature bath 13. The second stream of carrier gas flows from pre-column tubing 15 to empty column 17 and even through conduit means 19 to thermal conductivity detector 20. The response from detector 20 is collected over a specific time intervals between samplings and is stored in computer 30.

Constant temperature bath 13 may be subjected to an elevated temperature pulse in order to "bake out" columns 16 and 17 and remove tightly bound solute. The "bake-out" is accomplished by closing mechanical valves 24 and 25 from heated and cooled bath 23 and opening mechanical valves 27 and 28 to heated water bath 22. The water in heated bath 22 is maintained at an elevated or "bake-out" temperature of around 70° C. by a conventional thermostat. The heated water in bath 22 is pumped by pump 29 to constant temperature bath 13. This "bake-out" condition is continued for 24 hours to remove all residual solute in experimental column 16 before column 16 is subjected to a second experiment.

The calibration factor for converting the measurement of the concentration of the solute in the mobile phase passing downstream from the mass of the food to the amount of the solute in the mobile phase is calculated from the corresponding data from the runs using the empty column. Hence, the calibration factor or proportionality constant is determined from the known amount of solute in the mobile phase entering the empty column and the magnitude of the detector response measuring the concentration of solute in the mobile phase leaving the column.

Thereafter, the column bath temperature is stabilized at the desired run temperature. Solute is then injected into the experimental column. The run is monitored until the peak response has fallen to a level of about 10% of the peak height. The column bath temperature is raised from the experimental run temperature to the 70° C. "bake out" temperature. The run is terminated when the peak response falls to just above the baseline noise level and the data is filed on the hard drive.

The mass of water to be injected into the experimental column and the empty column is a predetermined excess quantity of water. The quantity is calculated to be at least twice the maximum amount which can be absorbed by the mass of the stationary phase when exposed to a water vapor saturated stream of carrier gas. With Avicel, a microcrystalline cellulose powder with almost no amorphous regions, a mass of water 5 to 10 times the maximum amount which the stationary phase can absorb is injected in a few injections to yield a prolonged exposure time. With sugar/dextrin containing foods, the quantity of water is about equal to the maximum amount of water which can be absorbed before sugar liquification occurs.

Carrier gases useful in the present invention include helium, nitrogen, carbon dioxide, oxygen, air and mixtures thereof. The carrier gas is maintained at a constant volume flow rate.

The temperature of the injector should be sufficiently high so as to substantially vaporize the predetermined quantity of solute to be injected into the port. For water, the temperature of the injector should be in the range of from about 150° to about 200° C.

Solutes useful in the present invention include any solute which may be absorbed by a food. These solutes include water, $C_3$–$C_6$ alcohols such as 2-propanol and 2-isopropanol, ketones such as acetone and methyl ethyl ketone, esters such as methylacetate, $C_5$–$C_{10}$ hydrocarbons such as hexane and aromatics such as toluene. Flavor and aroma components may also be used. Water is a preferred solute.

Foods useful in the present invention include foods which have moisture levels in the range of up to about 70%. These foods include but are not limited to proteins, carbohydrates, fats, salts and mixtures thereof.

The temperature of the column should be below the boiling point of the solute employed.

Detectors useful in the present invention include any detector which will detect and measure the solute used in the present invention. Preferred detectors are thermal conductivity detectors and flame ionization detectors.

The large excess of solute forms a broad band of solute saturated mobile phase passing downstream from pre-column tubing 14 to column 16. The term "transit width" is used to define the width of such a band. The transit width is the time from passage of the leading edge of the band to passage of the trailing end, multiplied by the downstream flow velocity. The transit width should be significantly greater than the length of the column. The combination of a short section of a column containing a stationary phase, a low temperature, a low flow rate and a high solute mass input relative to solid phase mass saturation, can provide a complete sorption isotherm profile ranging from essentially zero to a saturated solute partial pressure.

The post air peak to pre-curve peak area corresponds substantially to complete sorption of solute vapor by the stationary phase forming a plateau in the response curve. A drop in the maximum peak height is attained when the level of solute vapor in the carrier gas stream drops from a high (saturated) level to essentially zero.

The height of the detector response is directly proportional to the solute water vapor pressure, thereby providing a linear response in the detector. Since the uptake of solute is known, and the vapor pressure of the solute is also known at any one time, the kinetic relationship between the solute vapor in the mobile phase and the solute vapor in the stationary phase can be calculated.

Quantification of the sorption isotherm is based upon the following factors:

(1) The mass of solute input is a known quantity directly measured by the amount injected similar to conventional frontal chromatography where the known concentration of solute in carrier gas and known flow rate of carrier gas provide a calculated mass of solute.

(2) The detector response is proportional to the solute partial vapor pressure and is determined directly from the constant response plateaus at equilibrium of both the experimental column and the empty column. This external calibration method avoids the errors inherent in indirect calibration methods.

(3) The mass/area ratio may be determined directly from the known input of solute mass and the total area of the peak response. The accuracy of this ratio may be determined by injecting pulses of solute into the empty column. Errors arising from incomplete elution of solute mass may be avoided or measured by determining the difference in response areas of the injections of solute into the experimental column and the empty columns. Use of high temperature pulse elution aids in the quantification of the mass/area ratio even when incomplete elution was present at lower temperature.

The method of the present invention has great utility in gas/solid inverse chromatography because of the wide choice of interactions which may be studied. The only requirements in gas chromatography are that the stationary phase must be nonvolatile and the interacting solute must have a finite vapor pressure under the test conditions.

The method of the present invention also has great utility in liquid/solid inverse chromatography. The requirements in liquid chromatograph are that the stationary phase must be insoluble in the mobile phase. Ligands can also be used to provide a stationary phase when solubility problems exist.

Vapor uptake and vapor pressure equations were developed which incorporate an external calibration factor. This factor may be calculated from runs carried out with empty chromatographic columns and is specific only to temperature and the solute compound. The empty column external calibration provides the proportionality constants for sorption area response to mass of solute, and height of response to partial solute vapor pressure. Advantages of the present method are the simplicity of the technique combined with the accuracy that an external calibration factor offers, independent of substrate. By using an excess of solute sufficient to saturate both phases, a simple mass balance equation can then be used to calculate a sorption isotherm without the need to assume equilibrium is attained. Thus the presence of hysteresis error in conventional inverse gas chromatography can be avoided.

The following relations may be utilized:

$$\frac{H_1}{H_0} = \frac{P_1}{P_0} = A_w = R_h$$

wherein $A_w$=water activity, $R_h$=relative humidity, $P_1$=partial solute pressure at any plateau height response point $H_1$ in the sorption response, $H_0$=the plateau height response of empty column with $P_0$=partial solute pressure for pure solute at the specified column temperature in the empty column, and $$A = \frac{M_{p1} - K_a Y_1}{M}$$

where $M_{p1}$=mass injected or entering the sorbant by the time=$T_1$ (mass input into the column at a time corresponding to $H_1$), $K_a$=mass/area ratio, $Y_1$=area of response defined by the ramp front and $H_1$ at time $T_1$, A = solute absorbed per unit mass of solid sorbant at pressure $P_1$, and M = mass of solvent or solid phase.

$M_{p1}$ can be calculated from the transit time (or chart distance) corresponding to $H_1$ on the response curve by its ratio to the time for total elution, multiplied by the total mass injected or from a calibration obtained with an empty column. Thus a plot of mass injected versus total elution time gives a coefficient $K_t$. The product of $K_t$ and the time, to any specific point on the response curve, provides the mass $M_{p1}$ which has come into contact with the solid phase during that transit time. A simple procedure and a preferred embodiment to calculate the mass absorbed is to determine the difference between the total mass input of the solute at any time and the amount of solute not absorbed or eluted at that time. For a constant flow rate and constant input concentration ratio, as in the modified frontal method, the input is given by $K_t$ and the flow time. Unabsorbed or eluted mass is given by area $Y_1$ and the area/mass factor $K_a$. Thus $$A = \frac{K_t T_1 - K_a Y_1}{M}$$

$$P_1 = \frac{H_1}{H_0} P_0$$

These equations may be readily adapted to a data acquisition system based on an interfaced microcomputer with appropriate hardware for amplification and digitizing of the inverse gas chromatography input. Programs for integration and analysis of the data can be used.

The following example illustrates, but does not limit, certain aspects of the present invention:

EXAMPLE

Soluble Coffee

A 4 ounce jar of freeze-dried coffee and an 8 ounce jar of spray-dried coffee were passed through a 200 mesh screen. A portion of the spray dried coffee was also passed through a 400 mesh screen.

Corn Starch

Amioca, a high amylopectin/low amylose corn starch with less than 5% amylose content was obtained from the National Corn Starch and Chemical Company, Bridgewater, NJ.

Avicel

Avicel is a trademark of the FMC Corporation for their microcrystalline alpha cellulose.

Procedure

A short column, two to five centimeters long, by about 0.6 cm diameter, was used at 10% loading of food particulate matter, such as starch granules or ground coffee. A typical mass ratio was 100 mg of solid to about 100 ul of water, injected at a column temperature of about 25° C. The carrier gas flow rate was about 50 ml/min. The thermal conductivity detector operated initially at 0.01 millivolt sensitivity.

Appropriate scan rates, integration and sub-routines were provided to the computer to process the chromatographic data into the desired functions such as sorption isotherm, cluster function, partition coefficients, etc.

The data was obtained over a time course which included a preinjection period of zeroing the output and a post injection ramp period of increasing output response with a constant input concentration until the input and output partial pressures were equal. This ramp period was defined by the temperature and carrier flow rate and was followed by a desorption period of pure carrier gas until at least 90% of the solute input mass was exhausted from the solid phase. A post elution temperature rise may be used to clear the solid phase of residual solute if it is not temperature sensitive.

The experimental data obtained above with different starches and proteins show good agreement between static (weighing) and dynamic (inverse chromatography) sorption isotherms.

As these and other objects, features and advantages of the foregoing invention can be utilized without departing from the invention as defined in the claims, the foregoing description of the preferred embodiment should be taken by way of illustration rather than by way of limitation of the invention.

I claim:

1. A method for determining sorption isotherms of food by inverse chromatography comprising the steps of
   (a) passing a mobile phase having a known solute concentration and at a known flow rate through a stationary phase comprising a known mass of said food at a known temperature; and
   (b) measuring the concentration of said solute in said mobile phase passing a downstream of said stationary phase; and
   (c) determining the amount of said solute which has passed into said mass of said food at selected time intervals during said passing step from said known solute concentration, said known flow rate and the time elapsed since the beginning of said passing step; and
   (d) determining the amount of said solute in said mobile phase which has passed downstream from said mass of food at each of said selected time intervals during said passing step from said measurements of said concentration of said solute in said mobile phase; and
   (e) determining the amount of solute taken up by said food at each of said selected time intervals during said passing step from the difference in the amounts determined in steps (c) and (d).

2. The method according to claim 1 wherein said mobile phase includes a carrier gas.

3. The method according to claim 1 wherein said mobile phase is a carrier gas selected from the group consisting of helium, nitrogen, carbon dioxide, oxygen, air and mixtures thereof.

4. The method according to claim 1 wherein the known solute concentration is provided by flowing said mobile phase containing said solute through a tube maintained at a constant temperature containing pre-column tubing whereby the solute pressure in said mobile phase is a constant saturated pressure.

5. The method according to claim 4 wherein said constant temperature is a temperature wherein at least some of said solute in said mobile phase is condensed on said pre-column tubing.

6. The method according to claim 1 wherein said known temperature is a temperature below the boiling point of said solute.

7. The method according to claim 1 wherein said solute is selected from the group consisting of water, 2-normal-propanol, 2-isopropanol, acetone, methyl ethyl ketone, methyl acetate, hexane and toluene.

8. The method according to claim 7 wherein said solute is water.

9. The method according to claim 6 wherein said known temperature is a temperature below about 100° C.

10. The method according to claim 1 wherein said food is selected from the group consisting of carbohydrates, proteins, fats, salts and mixtures thereof.

11. The method according to claim 1 wherein said solute is measured with a thermal conductivity detector or a flame ionization detector.

12. The method according to claim 1 further including the step of providing a calibration factor for converting said measurement of said concentration of said solute in said mobile phase passing downstream from said mass of said food to said amount of said solute in said mobile phase comprising the steps of
   (a) passing a mobile phase having a known amount of solute through a substantially empty column at a known temperature; and
   (b) measuring the concentration of said solute in said mobile phase passing downstream of said empty column; and
   (c) determining the magnitude of the detector response in said measurements of said concentration of said solute in said mobile phase which has passed downstream from said empty column during said passing step; and
   (d) determining said calibration factor from the amounts in steps (a) and (c).

13. Apparatus for determining sorption isotherms of food by inverse chromatography comprising:
   (a) means for passing a mobile phase having a known solute concentration at a known flow rate in a downstream direction through a stationary phase comprising a known mass of a food while maintaining the mass of food at a known temperature, whereby the mobile phase will pass downstream from the mass of food;
   (b) means for measuring the concentration of said solute in the mobile phase passing downstream from the stationary phase;
   (c) means for determining the amount of said solute which has passed into the mass of food at selected time intervals during operation of said passing means from said known solute concentration, said known flow rate and the time elapsed since the beginning of passage of said mobile phase having known solute concentration into the mass of food;
   (d) means for determining the amount of said solute in said mobile phase which has passed downstream from the mass of food at each of said selected time intervals from said measurements of said concentration of said solute in said mobile phase; and
   (e) means for determining the amount of solute taken up by said food at each of said selected time intervals by determining the difference between the amount of solute which has passed into the mass of food and the amount of solute which has passed downstream from the mass of food.

14. The apparatus as claimed in claim 13 wherein said means for passing includes a source of mobile phase, a chromatograph chamber, means for maintaining said chromatograph chamber at a known temperature, a pre-column tubing disposed in said chromatograph chamber, conduit means for conducting mobile phase from said source to said pre-column tubing, an injection port for introducing a known amount of a solute into said mobile phase upstream of said pre-column tubing, and a column completed to said pre-column tubing and disposed in said chromatograph chamber for containing a stationary phase comprising food.

15. The apparatus according to claim 14 wherein said source of mobile phase is a source of a carrier gas.

16. The apparatus according to claim 15 wherein said source of mobile phase is a source of helium, nitrogen, carbon dioxide, oxygen, air and mixtures thereof.

17. The apparatus according to claim 14 wherein said temperature maintaining means is operative to maintain said chromatograph chamber at a temperature below the boiling point of said solute.

18. The apparatus according to claim 13 wherein the means for measuring concentration includes a thermal conductivity detector or a flame ionization detector.

19. The apparatus according to claim 14 further including an empty column disposed in said chromatograph chamber for calibration purposes.

* * * * *

UNITED STATES PATENT AND TRADEMARK OFFICE
CERTIFICATE OF CORRECTION

PATENT NO. : 4,869,093

DATED : September 26, 1989

INVENTOR(S) : Seymour G. Gilbert

It is certified that error appears in the above-identified patent and that said Letters Patent is hereby corrected as shown below:

Column 1, line 13, "insertion" should read --interaction--.
Column 5, line 32, "injection" should read --injector--.
Column 5, line 43, "belium" should read --helium--.
Column 9, line 57, "10%" should read --100%--.

Signed and Sealed this

Sixteenth Day of October, 1990

Attest:

HARRY F. MANBECK, JR.

Attesting Officer    Commissioner of Patents and Trademarks